United States Patent [19]

Nicolaou et al.

[11] Patent Number: 5,239,118

[45] Date of Patent: Aug. 24, 1993

[54] CYCLIC CONJUGATED ENEDIYNES

[75] Inventors: Kyriacos C. Nicolaou, Havertown; Guido Zuccharello, Philadelphia, both of Pa.; Yuji Ogawa, Tokyo, Japan

[73] Assignee: Trustees of the University of Penna., Philadelphia, Pa.

[21] Appl. No.: 803,618

[22] Filed: Dec. 9, 1991

Related U.S. Application Data

[62] Division of Ser. No. 214,019, Jun. 30, 1988, Pat. No. 5,097,062.

[51] Int. Cl.$^5$ ............................................. C07C 233/00
[52] U.S. Cl. ................................... 564/191; 564/152; 435/320.1; 435/964; 436/64; 436/128; 436/548; 536/55.1; 536/55.2; 536/45; 536/50

[58] Field of Search ............................... 564/152, 191; 435/320.1, 964; 436/64, 128, 548; 536/55.1, 55.2, 45, 50

[56] References Cited

PUBLICATIONS

Anon., Synform, 8(2), 90–112, 1990.
Singh, R. et al., Tetrahedron Lett., 31(2) 185–8, 1990.
Nicolaou, K. C. et al., J. Am. Chem. Soc. 110(21) 7247–48, 1988.

*Primary Examiner*—Paul J. Killos
*Attorney, Agent, or Firm*—Woodcock Washburn Kurtz Mackiewicz & Norris

[57] ABSTRACT

The synthesis of stable, ten-membered, cyclic conjugated enediynes is described. Said compounds were successfully employed to cleave double-stranded DNA spontaneously at ambient temperatures.

15 Claims, No Drawings

CYCLIC CONJUGATED ENEDIYNES

GOVERNMENT SUPPORT

Portions of this invention were supported by a grant from the National Science Foundation.

This is a division of application Ser. No. 214,019, filed Jun. 30, 1988, now U.S. Pat. No. 5,097,062.

BACKGROUND OF THE INVENTION

This invention relates to the cleavage of deoxyribonucleic acid (DNA) and, more specifically, to the cleavage of DNA by cyclic conjugated enediynes.

DNA is a very long, threadlike molecule which exists in the cells of all living organisms and which is intimately involved in the storage and transfer of genetic information. DNA is composed of discrete chemical units in a sequence unique to the particular organism from which it is derived.

DNA cleavage is currently a topic of considerable research investigation, due in a large part to the recognition that certain molecules interact and bind with sites on a DNA molecule on the basis of the site's specific chemical sequence. The sequence-specific cleavage of DNA is essential for many techniques in molecular biology, including gene isolation, DNA sequence determination, and recombinant DNA manipulation. Presently, such cleavage is performed largely with naturally-occurring restriction enzymes which bind and cleave DNA at particularly sequenced sites. However, because both the number and sequence specificities of such enzymes are limited, it is only possible to cleave DNA at a fixed number of recognition sites. It would be of great advantage, however, to be able to cleave DNA at any predetermined site; the design of sequence-specific DNA cleaving molecules that go beyond the specificities of natural enzymes might provide this capability. The ability to design molecules with predetermined specificities for selective cleavage would be of great importance for drug design, molecular biology, and materials chemistry.

The capability to selectively target particularly sequenced site on DNA and modify it in some manner may provide a means of treatment for a disease or condition controlled by that site. For example, it has long been the desire of medicine to kill cancer cells in man. Conceivably, such cells might be killed if their DNA were properly cleaved. A number of molecules are known to facilitate DNA strand cleavage; however, many such compounds are believed to attack DNA in a non-selective fashion. Because of the toxic nature of such non-selective DNA-reactive compounds, medicinal therapies which employ them have generally been reserved for advanced forms of cancer and other life-threatening diseases. With the advent of molecules which can selectively bind and cleave cancer cell DNA on the basis of a particular chemical sequence, new methods for the design of safe, effective, and highly specific therapeutic anticancer agents might be developed. Much effort has therefore been directed toward the development of molecules that target and cleave chemically specific sites along a strand of DNA. Both naturally-occurring and synthetic compounds have demonstrated the ability to cleave DNA under certain conditions; however, the presence of other reactive species has in many cases been necessary to effect the desired cleavage. The recently reported calichemicin and esperimicin classes of antibiotics are novel naturally occurring compounds with unusually high potency against murine tumors. This potent antitumor activity has been attributed to the demonstrated ability of compounds of these classes to induce double-stranded DNA cleavage. However, the mode of action for compounds belonging to these classes is thought to depend upon the attack of some nucleophilic species. After recognition and interaction of a given molecule with DNA, the nucleophile is thought to trigger a sequence of intramolecular reactions centering on the bicyclic core structure characteristic of the calichemicin/esperimicin class. These reactions are believed to generate a highly reactive benzenoid diradical species through the cyclization of the conjugated enediyne moiety present within the bicyclic core. This species, in turn, is thought to react with and damage DNA's phosphate backbone.

The calichemicin/esperimicin class are characterized by large, complex molecular frameworks. A number of smaller molecules modeled after these antibiotics have been reported. Schreiber and Kiessling, *J. Am. Chem. Soc.*, 110, 631 (1988), have described a procedure for the synthesis of bicyclic molecules comprising a conjugated enediyne moiety and a bridgehead double bond whose saturation is believed to play a central role in the mechanism for DNA cleavage. Magnus and Carter, *J. Am. Chem. Soc.*, 110, 1625 (1988), have reported the synthesis of a cyclic cobalt complex which they hypothesize to generate—as a nonisolable intermediate—a bicyclic system similar to that of the calichemicin/esperimicin class, but differing in that its bridgehead position is already saturated. It is believed that this nonisolable intermediate generates benzenoid diradicals by way of a cyclization involving conjugated enediyne functionality.

Although the discussed calichemicin/esperimicin model systems have been constructed, no associated DNA-cleaving properties associated have been reported.

It has been widely hypothesized that the carbon-carbon double bond at the bridgehead of the discussed bicyclic system is a key element in the mode of action of the calichemicin/esperimicin class and a key determinant of any similar activity exhibited by systems modeled after them. This double bond locks the molecules into a certain geometry and prevents the ends of the diyne from approaching one another closely enough for cyclization and diradical generation to occur. Therefore, an intramolecular addition reaction which changes the double bond to a single bond—and thus allows molecular geometries suitable for cyclization—is thought to be a necessary first step in the DNA cleaving action of compounds incorporating such a bicyclic system into their molecular framework.

SUMMARY OF THE INVENTION

This invention provides for the preparation and use of compounds which mimic the DNA-cleaving properties of the calichemicin/esperimicin class of antibiotics. Because the characteristic bicyclic core of the calichemicin/esperimicin class is not present within the structures of the compounds of this invention, their activity is dependent upon neither the occurrence of an intramolecular addition reaction nor the presence of other reactive chemical species. This invention is more particularly pointed out in the appended claims and described in it preferred embodiments in the following description.

DETAILED DESCRIPTION OF THE INVENTION

The primary compounds of this invention are conjugated cyclodecaenediynes having general structure (1):

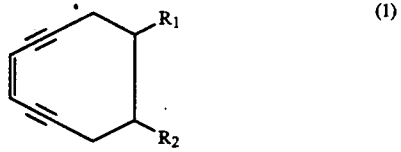

where $R_1$ and $R_2$ can be the same or different and are selected from the group consisting of —CH$_2$OC(O)CH$_3$, —C(O)NHR$_3$, —(CH$_2$)$_n$OH, —(CH$_2$)$_n$O—saccharides, —(CH$_2$)$_n$O-DNA intercalators, —(CH$_2$)$_n$O-DNA minor groove binders, —(CH$_2$)$_n$O-DNA binding proteins, —(CH$_2$)$_n$O-DNA fragments, —(CH$_2$)$_n$O-RNA fragments, or —(CH$_2$)$_n$O-monoclonal antibodies, where n=1-10, preferably 1-5 and $R_3$ is selected from the group consisting of saccharides, DNA intercalators, DNA minor groove binders, DNA binding proteins, DNA fragments, RNA fragments, or monoclonal antibodies. Representative sugars include glucose, galactose, and 6-deoxygalactose. Representative DNA intercalators include acridine, ethidium bromide, quinacrene, and phenanthridine. Representative DNA minor groove binders include distamycin and netropsin. Representative DNA binding proteins include tryptophan gene repressor, Hin recombinase, and Hin 52mer binding fragment. Representative monoclonal antibodies include mAb 9.2.27 (Ig G2a).

These conjugated cyclodecaenediynes are designed as DNA cleaving molecules. An important feature is that they are sufficiently stable at ambient temperatures to allow their isolation and handling, but that they undergo cyclization at 37° C. (body temperature) to benzenoid diradicals at useful rates to cleave DNA.

For compounds of this invention, the hydrogen atoms attached to the two bridgehead carbons of the cyclodecaenediyne can be on the same side of the molecule "cis" with respect to one another), as given by structure (2), or on opposite sides of the molecule ("trans" with respect to one another) as given by structure (3).

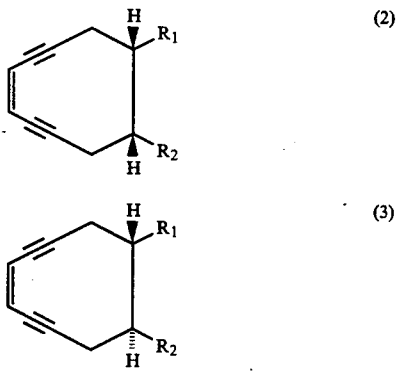

Compounds of this invention are prepared generally from 1,2-disubstituted 4-cyclohexenes such as (cis)-1,2-dihydroxymethyl-4-cyclohexene. The particular substitution pattern of a given cyclohexene is chosen with an eye toward both the ultimate cyclodecaenediyne product desired and the interaction of that product's substituents with a particular targeted site along the DNA molecule. Sensitive functionality present within the chosen cyclohexene starting material might, however, prove unstable under the reaction conditions employed in synthesizing the cyclodecaenediyne. Thus, reactive functionality should be shielded from subsequent reaction conditions through the use of appropriately-chosen protecting groups which may be removed as desired at some later stage of the synthesis. For example, to protect the hydroxyl groups in structure (4) from the conditions to which it would otherwise be exposed in the synthesis of structure (12), it may be reacted with tert-butyldiphenylsilyl chloride under basic conditions to yield the silyl derivative of structure (5), where X=—Si(C$_6$H$_5$)$_2$C(CH$_3$)$_3$.

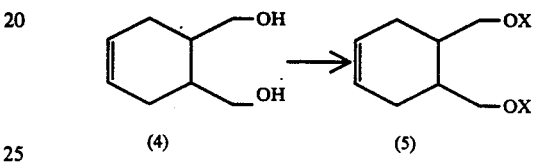

Cleavage of the carbon-carbon double bond in structure (5) to yield terminal carbonyls may then be performed; for example, treatment of structure (5) with ozone in ethyl acetate and methanol, then trimethyl phosphite yielded structure (6).

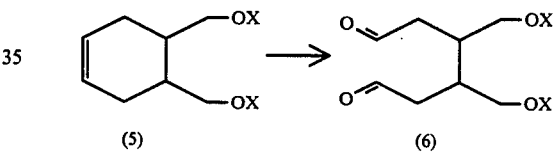

Compounds such as structure (6) are then reacted with carbon tetrabromide and triphenylphosphine in methylene chloride, for example, to yield dihalo olefins as in structure (7),

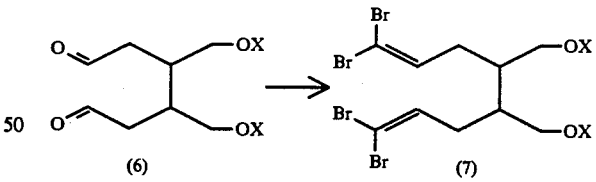

which may be treated with n-butyllithium and methyl chloroformate in tetrahydrofuran, then diisobutylalunium hydride in methylene chloride, then trioctylphosphine and carbon tetrabromide in diethyl ether to yield di-acetylenic compounds such as structure (8).

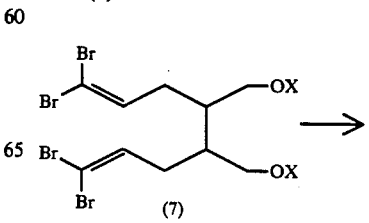

Compounds like structure (8) may then be reacted with sodium sulfide nonahtydrate in ethanol and water to yield cyclic sulfides such as structure (9), which are converted to alpha-halo sulfones, as is structure (9) by treating it with 3-chloroperbenzoic acid in methylene chloride, then sulfuryl chloride and pyridine in methylene chloride, then 3-chloroperbenzoic acid in methylene chloride.

Treatment of compounds similar to structure (10) with bases like methyllithium in solvents such as diethyl ether yields the cyclic conjugated enediyne moiety of structure (11).

The particular protecting groups employed to protect reactive functionality are then removed, as the silyl groups of structure (11) are removed with tetrabutylammonium fluoride in tetrahydrofuran, yielding the conjugated cyclodecaenediyne diol of structure (12).

To engender site selective cleavage of DNA, many different types of chemical functionality can conceivably be appended to the cyclodecaenediyne core common to compounds of this invention, and such functionality can be chosen as appropriate for any number of DNA cleaving applications. One method of adapting the conjugated cyclodecaenediyne core to a specific cleavage application is to select as starting material a cyclohexene comprising much or all of the functionality desired in the ultimate product. Examples 1, 2, and 3 follow this methodology for functionalizing the basic core structure of this invention and for using the respective functionalized compounds to cleave DNA.

The cyclodecaenediyne core may also be modified for a particular desired site-specific cleavage by first synthesizing a relatively simple cyclodecaenediyne, such as the diol of structure (12), and then attaching to it any desired functionality. An example of this methodology for synthesizing and using modified cyclodecaenediynes is given by Example 4.

The invention will now be described in connection with the following examples thereof wherein parts and percents are by weight unless otherwise specified.

EXAMPLE 1

A. Preparation of a compound of structure (1) where $R_1=R_2=-CH_2OH$, (cis)-1,2,-dihydroxymethyl-cyclodeca-6-ene-4,8-diyne Imidazole (107 grams) was added to a solution of 750 milliliters dimethylformamide, 89 grams (cis)-1,2-dihydroxymethyl-4-cyclohexene (structure (4)), and 343 grams tert-butyldiphenylsilyl chloride; the resultant mixture was allowed to stir for 10 hours. The mixture was then poured into 1.0 liter of water and 1.0 liter of diethyl ether; the solution was then stirred for 30 minutes. The organic layer was separated, washed with 1.0 liter of water then 1.0 liter saturated sodium chloride solution, dried over magnesium sulfate, and concentrated. The concentrate was then flash column chromatographed (SiO$_2$, 0–10% diethyl ether in petroleum ether) and the solvent evaporated to yield 178 grams of a white, dense solid corresponding to structure (5). A solution comprising 48 grams of this solid, 400 milliliters diethyl ether, and 100 milliliters methanol was cooled to $-78°$ C.; ozone was bubbled through the solution for four hours. Trimethyl phosphite (20 grams) was then added and the reaction was allowed to warm to room temperature. The solvent was removed and the residue was dissolved in 300 milliliters methylene chloride, washed with 100 milliliters of water, dried over magnesium sulfate, and concentrated. It was then dissolved in 40 milliliters methylene chloride and added to a cooled (0° C.) solution of 110 grams triphenylphosphine and 69.5 grams carbon tetrabromide which had been stirring for 30 minutes. The solution was then allowed to warm to room temperature and stirring was maintained for 12 hours. The reaction was then concentrated and the triphenylphosphine oxide was precipitated by treating the residue twice with 200 milliliter portions of a 60% solution of diethyl ether in petroleum ether. The mother liquors were then concentrated, treated with 200 milliliters petroleum ether, filtered, and flash column chromatographed (SiO$_2$, 0–2.5% diethyl ether in petroleum ether). The solvent was evaporated to give 42 grams of a white solid corresponding to structure (7).

To a cooled (-78° C.) solution of this solid (32 grams) in 300 milliliters tetrahydrofuran was added n-butyllithium (27 milliliters of a 1.6 molar hexane solution). After 30 minutes the solution was transferred via cannula to a cooled (0° C) solution of methyl chloroformate (33 grams) in 250 milliliters of tetrahydrofuran. After an additional 45 minutes of stirring, 150 milliliters saturated ammonium chloride solution was added and the organic layer was washed with 50 milliliters saturated sodium chloride solution, dried over magnesium sulfate, and concentrated. The crude product was then recrystallized from ethyl acetate/hexane 1:3) to give 18.5 grams of a white, crystalline solid.

To a cooled (−78° C.) solution of this solid (19.5 grams) in 600 milliliters of methylene chloride was added diisobutylaluminum hydride (175 milliliters of a 1.0 molar methylene chloride solution). This mixture was allowed to warm to 5° C. over 2.5 hours. Then 3.0 milliliters methanol and 100 milliliters saturated sodium potassium tartrate were added and the reaction was stirred for 30 minutes. The aqueous layer was then extracted with 300 milliliters ethyl acetate. The combined organic portions were then dried over magnesium sulfate and concentrated to give 21.9 grams of an almost pure white solid residue.

To a cooled (0° C.) solution of this solid residue (21.9 grams) and carbon tetrabromide (22.7 grams) in 400 ml diethyl ether was added trioctylphospine (26.4 grams). The cooling bath was then removed and after 1 hour more trioctylphosphine (8.2 grams) was added. After 15 minutes another 8.2 grams portion of trioctylphosphine was added. Ten minutes later, the solvent was removed and the crude reaction mixture was flash column chromatographed (SiO$_2$, 0–25% methylene chloride in petroleum ether). The mixed fractions obtained were then concentrated, flash column chromatographed (SiO$_2$, 1–20% ether in petroleum ether), and the solvent evaporated to give 27 grams of a white solid corresponding to structure (8).

To a suspension of this solid (8.1 grams) in 450 milliliters ethanol was added 16.3 grams sodium sulfide nonahydrate in 90 milliliters water. The reaction was heated to reflux for 30 minutes and then stirred for an additional 30 minutes. The reaction mixture was then concentrated to 50 milliliters and added to 250 milliliters of diethyl ether and 150 milliliters of saturated ammonium chloride solution. The organic phase was then washed with 100 milliliters of saturated sodium chloride solution, dried over magnesium sulfate, and concentrated. It was then flash column chromatographed (SiO$_2$, 4:1-1:1, petroleum ether:methylene chloride) and the solvent evaporated to give 2.98 grams of a white solid corresponding to structure (9); R$_f$=0.60 (SiO$_2$, 25% methylene chloride in petroleum ether); $^1$H NMR (250 MHz, CDCl$_3$) sigma 7.63 (m, 8 H, phenyl), 7.35 (m, 12 H, phenyl), 3.70 (m, 4 H, C$\underline{H}_2$-O), 3.30 (d, J=2.3 Hz, 4 H, C$\underline{H}_2$-S), 2.32 (m, 4 H, C$\underline{H}_2$), 1.98 (m, 2 H, C$\underline{H}$), 1.01 (s, 18 H, CH$_3$).

To a cooled (−30° C.) solution of this solid (8.9 grams) in 500 milliliters methylene chloride was added 3-chloroperbenzoic acid (85% pure, 2.6 grams). After 40 minutes, 2 milliliters of methyl sulfide was added and the reaction was warmed to room temperature. The product was then extracted with 150 milliliters saturated sodium bicarbonate solution and 100 milliliters saturated sodium chloride solution, dried over magnesium sulfate, and concentrated. It was then flash column chromatographed (SiO$_2$, 80–100% diethyl ether in petroleum ether) and the solvent evaporated to give 8.23 grams of a pure, white, crystalline, solid residue.

To a cooled (−78° C.) solution of this solid residue (7.5 grams) and pyridine (2.9 grams) in 200 milliliters methylene chloride was added sulfuryl chloride (1.6 grams). After 30 minutes, 10 milliliters of saturated ammonium chloride solution was added; the reaction was then warmed to room temperature. The organic layer was washed with 100 milliliters saturated sodium bicarbonate solution, 100 milliliters saturated sodium choloride solution, dried over magnesium chloride, and concentrated. It was then flash column chromatographed (SiO$_2$, 0–10% ethyl acetate in methylene chloride) and the solvent evaporated to give 6.20 grams white solid residue.

To a cooled (0° C.) solution of this solid residue (6.2 grams) in 200 milliliters methylene chloride was added 3-chloroperbenzoic acid (5.6 grams). The reaction was allowed to warm to room temperature and was stirred for 18 hours. Then 5 milliliters of methyl sulfide was added and the reaction was washed with 100 milliliters saturated sodium bicarbonate solution and 100 milliliters saturated sodium chloride solution, dried over magnesium sulfate, and concentrated to give 6.25 grams of an orange-tan solid corresponding to structure (10); R$_f$=0.18 (SiO$_2$, 30% diethyl ether in petroleum ether); $^1$H NMR (250 MHz, CDCl$_3$) sigma 7.61 (m, 8 H, phenyl), 7.38 (m, 12 H, phenyl) 5.19 (m, 1 H, C$\underline{H}$-Cl), 4.47 (m, 1 H, SO$_2$-C$\underline{H}_2$), 3.74 (m, 1 H, SO$_2$-C$\underline{H}_2$), 3.62 (m, 4 H, C$\underline{H}_2$-O), 2.36 (m, 4 H, C-C$\underline{H}_2$), 1.94 (m, 2 H, C$\underline{H}$), 1.01 (s, 18 H, CH$_3$).

To a cooled (−78° C.) solution of methyllithium (5.0 milliliters of a 1.29 molar diethyl ether solution) in 250 milliliters diethyl ether was added a cooled (−78° C.) solution of this solid (4.0 grams) in 70 milliliters of diethyl ether. After 15 minutes, 50 milliliters of saturated ammonium chloride solution was added and the cooling bath removed. The reaction was then washed with 50 milliliters saturated sodium chloride solution, dried over magnesium sulfate, and concentrated. It was twice flashed column chromatographed (SiO$_2$, 5% diethyl ether in petroleum ether), then purified by preparative thin-layer chromatography (SiO$_2$, 5% diethyl ether in petroleum ether), and the solvent evaporated to give 0.169 grams of a white, crystalline solid corresponding to structure 11; R$_f$=0.39 (SiO$_2$, 5% diethyl ether in petroleum ether); $^1$H NMR (250 MHz, CDCl$_3$) sigma 7.61 (m, 8 H, phenyl), 7.33 (m, 12 H, phenyl), 5.77 (s, 1 H, olefinic), 3.78 (m, 4 H, C$\underline{H}_2$-0), 2.57 (dd, J=6.3, 18.0 Hz, 2 H, C-C$\underline{H}_2$), 2.49 (dd, J=3.0, 17.8 HZ, 2 H, C-C$\underline{H}_2$), 2.18 (m, 2 H, C$\underline{H}$), 1.10 (s, 18 H, CH$_3$).

To a solution of this solid (45 milligrams) in 2 milliliters of tetrahydrofuran was added tetrabutylammonium fluoride (0.3 milliliters of a 1.0 molar tetrahydrofuran solution). This was stirred for 30 minutes and then, after 1.0 milliliter of toluene was added, all solvent was removed. The residue was then flash column chromatographed (SiO$_2$, 5% methanol in methylene chloride) and the solvent evaporated to give 10 milligrams of a white, amorphous solid corresponding to structure (12); R$_f$=0.24 (SiO$_2$, 5% methanol in methylene chloride); $^1$H NMR (250 MHz, CD$_3$OD-D$_2$O, 15:85) sigma 5.89 (s, 2H, olefinic), 3.72 (m, 4 H, CH$_2$-O), 2.51 (m, 4 H, C-CH$_2$), 2.10 (m, 2 H, CH).

B. Cleavage of DNA with the compound

To a vial containing a 50 micromolar per base pair solution of φX174 Type I double-stranded DNA in 2 microliters pH 8.5 tris-HCl buffer was added 6.0 microliters of a pH 8.5 tris-HCl buffer solution and 2.0 microliters of a 5.0 micromolar aqueous solution of (cis)-1,2-dihydroxymethyl-cyclodeca-6-ene-4,8-diyne. The vial was then placed in a 37° C. oven for 24 hours; 2.0 microliters of glycerol loading buffer solution containing bromothymol blue indicator was added and a 10 microliter aliquot was drawn. Gel electrophoresis analysis of the aliquot was then performed using a 1.0% agarose gel with ethidium bromide run at 115 volts for one hour. DNA cleavage was indicated by the formation of Type II DNA, which was detected by visual inspection of the gel under 310 nanometer ultraviolet light.

EXAMPLE 2

A. Preparation of a compound of structure (11 where R$_1$=R$_2$=—CH$_2$CH$_2$OH, (cis)-1,2-di(2-hydroxyethyl)-cyclodeca-6-ene-4,8-diyne To a cooled (−78° C.) solution of oxalyl chloride (233 grams) in 600 milliliters methylene chloride is added dimethyl sulfoxide (250 grams). After 10 minutes, 89 grams (cis)-1,2-dihydroxymethyl-4-cyclohexene (structure (4)) is added; 15 minutes later triethylamine (700 grams) is added. After 45 minutes, the cooling bath is removed; 30 minutes later 2.0 liters 5% hydrochloric acid solution is added. The organic layer is then extracted with 500 milliliters saturated sodium bicarbonate, 500 milliliters of water, and 500 milliliters saturated sodium chloride solution, dried over magnesium sulfate, and concentrated to a solid residue.

Sodium hydride (62 grams of a 50% dispersion in mineral oil) is added to 500 milliliters of dry dimethyl sulfoxide, and the mixture is warmed to 55° C. for 30 minutes. Then ethoxymethylene triphenylphosphonium chloride (500 grams) in 500 milliliters dimethyl sulfoxide is added. After 30 minutes, a solution of the solid residue (87 grams) in 500 milliliters of dimethyl sulfoxide is added and the reaction is heated to 70° C. for 10 hours. It is then poured into 2.0 liters of water and extracted with two 500 milliliter portions of ethyl acetate. The organic layer is then dried over magnesium sulfate, concentrated, and dissolved in 1 0 liters diethyl ether. Then 500 milliliters of 70% perchloric acid is added and the mixture is stirred for 10 hours. It is then poured into 1.0 liters saturated sodium bicarbonate solution, extracted with two 1.0 liter portions of ethyl acetate, dried over magnesium sulfate, and concentrated to a solid residue.

To this solid residue (107 grams) in 600 milliliters of methanol is added sodium borohydride (22 grams) and the mixture is allowed to stir for 3 hours. Then it is poured into 1.0 liters 1.0 normal hydrochloric acid, extracted with three 500 milliliter portions of ethyl acetate, dried over magnesium sulfate, and concentrated to yield (cis)-1,2-di(2-hydroxyethy)1-4-cyclohexene as a solid residue.

The method of Example 1, Section A is then followed, except that 109 grams (cis)-1 ,2-di(2-hydroxyethyl)-4-cyclohexene is used in place of 89 grams (cis)-1,2-dihydroxymethyl-4-cyclohexene.

B Cleavage of DNA with the compound

The method of Example 1, Section B is followed except that (cis)-1,2-di(2-hydroxyethyl)-cyclodeca-6-ene-4,8-diyne is employed in place of (cis)-1,2-dihydroxymethyl-cyclodeca-6-ene-4,8-diyne.

EXAMPLE 3

A Preparation of the compound of structure where R$_1$- R$_2$=CH$_2$OH. (trans)-1.2-dihydroxymethyl-cyclodeca-6-ene-4,8-diyne The method of Example 1, Section A is followed except that (trans)-1,2-dihydroxymethyl-4-cyclohexene is used in place of (cis)-1,2-dihydroxymethyl-4-cyclohexene.

B. Cleavage of DNA with the compound

The method of Example 1, Section B is followed except that (trans)-1,2-dihydroxymethyl-cyclodeca-6-ene-4,8-diyne is employed in place of (cis)-1,2-dihydroxymethyl-cyclodeca-6-ene-4,8-diyne.

EXAMPLE 4

Preparation of the compound of structure (1where R$_1$=R$_2$=—CH$_2$O-glucose, (cis)-1,2-di-[[(diolucopyranosyl) oxy]methy]cyclodeca-6-ene-4,8-diyne To a solution of (cis)-1,2-dihydroxymethyl-cyclodeca-6ene-4,8-diyne structure (12)) (1.0 grams) and sugar acetamidate 2,3,4,6-tetra-O-[(1,1-dimethylethyl) dimethylsilyl]glucopyranose 1-(1,1-trichloro)acetamidate) (8.0 grams) in 30 milliliters of benzene is added pyridinium para-toluene sulfonate (0.40 grams). After 3 hours stirring, the mixture is poured into 10 milliliters saturated sodium bicarbonate solution. The organic layer is then washed with 10 milliliters saturated sodium chloride solution, dried over magnesium sulfate, and concentrated to a solid residue.

To a solution of this solid residue (1.0 grams) in 3.0 milliliters of tetrahydrofuran is added tetrabutylammonium fluoride (22 milliliters of a 1.0 molar tetrahydrofuran solution). After 3 hours the solvent is removed to give a solid residue.

B. Cleavage of DNA with the compound

The method of Example 1, Section B is followed except that (cis)-1,2-di-[[(diglucopyranosyl)oxy]methyl]cyclodeca-6-ene-4,8-diyne is employed in place of (cis)-1,2-dihydroxymethyl-cyclodeca-6-ene-4,8-diyne.

The products of DNA cleavage presently have great utility in biomedical research. For example, DNA cleavage currently provides a means of constructing new combinations of genes in the laboratory. These novel genes can then be inserted into suitable host cells and cloned by the DNA-synthesizing system of the host. The employment of DNA cleavage products in this manner has resulted in the synthesis of large quantities of otherwise scarce proteins by such clones. DNA cleavage is also a vital step in the process embodied by U.S. Pat. No. 4,736,866, Leder et al., for the creation of genetically altered mice. This process employs enzymatic techniques to cleave DNA. As mentioned, enzymatic techniques have limitations which might well be overcome by the development of site-specific synthetic molecules which could be coupled with the compounds of this invention to enable DNA cleavage at a wider variety of sites than is presently available.

The results of the provided examples confirm that the simple cyclic conjugated enediynes of this invention spontaneously cleave DNA. In addition, it is suspected that alpha-halo sulfones, similar to structure (10) but having substituents at the bridgehead positions as defined for $R_1$ and $R_2$ above, may also exhibit DNA cleaving properties; the mode of action of such compounds may involve a transformation to cyclodecaenediynes. Incorporation of the core structure of structure (1) or of related structures into molecular assemblies carrying suitable site-specific moieties can result in powerful biotechnology reagents; they may also be useful therapeutic agents for the treatment of cancer and other diseases.

We claim:

1. A chemical compound having the structure:

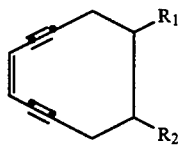

wherein $R_1$ and $R_2$ are the same or different and are selected from the group consisting of —C(O)NHR$_3$, —(CH$_2$)$_n$O-saccharides, —(CH$_2$)$_n$O-DNA intercalators, —(CH$_2$)$_n$O-DNA minor groove binders, —(CH$_2$)$_n$O-DNA binding proteins, —(CH$_2$)$_n$O-DNA fragments, —(CH$_2$)$_n$O-RNA fragments, or —(CH$_2$)$_n$O-monoclonal antibodies, where n=1-10, preferably 1-5 and $R_3$ is selected from the group consisting of saccharides, DNA intercalators, DNA minor groove binders, DNA binding proteins, DNA fragments, RNA fragments, or monoclonal antibodies.

2. The chemical compound of claim 1 wherein the hydrogens on the bridgehead carbons are in the cis configuration.

3. The chemical compound of claim 1 wherein the hydrogens on the bridgehead carbons are in the trans configuration.

4. The chemical compound of claim 1 wherein either $R_1$ or $R_2$, or both of them, is —CH$_2$O-glucose.

5. The chemical compound of claim 1 wherein either $R_1$ or $R_2$, or both of them, is —CH$_2$O-glucose and the hydrogens on the bridgehead carbons are in the cis configuration.

6. A method of cleaving DNA comprising contacting the DNA molecule to be cleaved with the compound of claim 1.

7. The method of claim 6, wherein $R_1$ and $R_2$ of the compound of claim 1 are —CH$_2$O-glucose.

8. A method of preparing the chemical compound of claim 1 comprising:

a) cleaving the carbon-carbon double bond of a chemical compound having the structure:

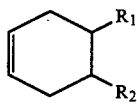

where $R_1$ and $R_2$ are defined as in claim 1, to form two terminal aldehyde groups at the points of cleavage, b) reacting the dialdehyde product of step (a) with carbon tetrabromide to produce two terminal dibromo olefin groups, c) converting the terminal olefin groups of the product of step (b) to acetylenic groups bearing terminal dihalomethyl groups, d) cyclizing the diacetylenic product of step (c) with a sulfur-containing compound to yield an eleven-membered cyclic sulfide, e) converting the cyclic sulfide of step (d) to an eleven-membered cyclic alpha-halo sulfone, and f) treating the alpha-halo sulfone of step (e) with a base to produce the chemical compound of claim 1.

9. A method of preparing the chemical compound of claim 1 comprising:

a) reacting a chemical compound having the structure:

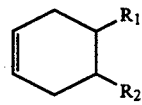

where $R_1$ and $R_2$ are defined as in claim 1, with ozone and then trimethyl phosphite to effect the cleavage of the carbon-carbon double bond and the formation of two aldehyde groups, b) reacting the dialdehyde product of step (a) with carbon tetrabromide and triphenylphosphine to add one carbon to each of the aldehydes and to produce terminal dibromo olefin groups, c) converting the terminal olefin groups of the product of step (b) to acetylenic groups bearing terminal dihalomethyl groups by treating the olefinic product of step (b) with n-butyllithium and methyl chloroformate, then diisobutylaluminum hydride, then trimethyl phosphite and carbon tetrahalide, d) reacting the diacetylenic product of step c) with sodium sulfide nonahydrate to yield an eleven membered cyclic sulfide, e) contacting the cyclic sulfide of step d) with 3-chloroperbenzoic acid, then sulfuryl chloride and pyridine, then 3-chloroperbenzoic acid to produce an eleven membered cyclic alpha-chloro sulfone, and f) contacting the alpha-chloro sulfone of step (e) with methyllithium to produce the compound of claim 1.

10. A method of preparing the chemical compounds of claim 1 comprising reacting a cyclic alpha-halo sulfone of the structure:

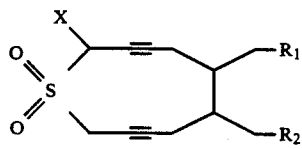

wherein X is F, Cl, Br, or I, with a base.

11. The method of claim 10, wherein X is Cl.

12. The method of claim 10, wherein the base is methyllithium.

13. The method of claim 10 wherein X is Cl and the base is methyllithium.

14. A method of preparing the compound of claim 1 comprising reacting a compound of structure:

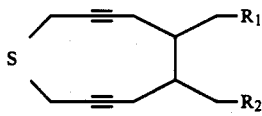

with 3-chloroperbenzoic acid, then sulfuryl chloride, then 3-chloroperbenzoic acid to produce a compound of structure:

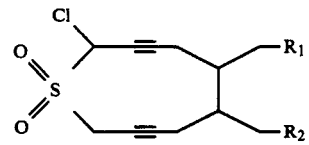

and then treating that compound with a base.

15. The method of claim 14 wherein the base is methyllithium.

* * * * *